(12) United States Patent
Zucker et al.

(10) Patent No.: US 8,603,112 B2
(45) Date of Patent: Dec. 10, 2013

(54) SUTURING ASSEMBLY AND METHOD

(75) Inventors: Ygal Zucker, Haifa (IL); Einat Duvdevany Fabian, Kfar Truman (IL); Nir Altman, Kibbutz Kfar Etzion (IL)

(73) Assignee: EasyLap Ltd., Kfar Truman (IL)

( * ) Notice: Subject to any disclaimer, the term of this patent is extended or adjusted under 35 U.S.C. 154(b) by 1313 days.

(21) Appl. No.: 11/947,798

(22) Filed: Nov. 30, 2007

(65) Prior Publication Data

US 2009/0143790 A1    Jun. 4, 2009

(51) Int. Cl.
    *A61B 17/04* (2006.01)
(52) U.S. Cl.
    USPC .......................................... 606/144; 606/148
(58) Field of Classification Search
    USPC ...................... 606/1, 139, 144–150
    See application file for complete search history.

(56) References Cited

U.S. PATENT DOCUMENTS

| 5,222,977 | A | * | 6/1993 | Esser | 606/223 |
|---|---|---|---|---|---|
| 5,250,055 | A | * | 10/1993 | Moore et al. | 606/148 |
| 5,281,237 | A | * | 1/1994 | Gimpelson | 606/144 |
| 5,336,231 | A | * | 8/1994 | Adair | 606/148 |
| 5,462,560 | A | * | 10/1995 | Stevens | 606/144 |
| 5,468,251 | A | * | 11/1995 | Buelna | 606/223 |
| 5,496,332 | A | * | 3/1996 | Sierra et al. | 606/139 |
| 5,665,096 | A | * | 9/1997 | Yoon | 606/139 |
| 5,713,908 | A |   | 2/1998 | Jameel et al. |   |
| 5,749,879 | A | * | 5/1998 | Middleman et al. | 606/139 |
| 5,782,845 | A | * | 7/1998 | Shewchuk | 606/144 |
| 5,817,107 | A | * | 10/1998 | Schaller | 606/139 |
| 5,817,111 | A | * | 10/1998 | Riza | 606/148 |
| 5,860,990 | A | * | 1/1999 | Nobles et al. | 606/144 |
| 5,895,395 | A | * | 4/1999 | Yeung | 606/144 |
| 5,972,005 | A | * | 10/1999 | Stalker et al. | 606/144 |
| 6,074,404 | A | * | 6/2000 | Stalker et al. | 606/144 |
| 6,562,052 | B2 | * | 5/2003 | Nobles et al. | 606/144 |
| 6,638,286 | B1 | * | 10/2003 | Burbank et al. | 606/157 |
| 6,716,224 | B2 | * | 4/2004 | Singhatat | 606/148 |
| 6,723,107 | B1 | * | 4/2004 | Skiba et al. | 606/144 |
| 7,270,672 | B1 | * | 9/2007 | Singer | 606/148 |
| 7,306,613 | B2 | * | 12/2007 | Kawashima et al. | 606/148 |
| 7,625,386 | B2 | * | 12/2009 | Abe et al. | 606/144 |
| 8,313,509 | B2 | * | 11/2012 | Kostrzewski | 606/232 |
| 2003/0004544 | A1 | * | 1/2003 | Kawashima et al. | 606/222 |
| 2003/0233106 | A1 | * | 12/2003 | Dreyfuss | 606/144 |
| 2004/0249393 | A1 | * | 12/2004 | Weisel et al. | 606/144 |
| 2007/0118153 | A1 | * | 5/2007 | Funamura et al. | 606/148 |
| 2007/0179509 | A1 | * | 8/2007 | Nagata et al. | 606/144 |
| 2007/0219567 | A1 | * | 9/2007 | Bayer et al. | 606/148 |

(Continued)

FOREIGN PATENT DOCUMENTS

| EP | 1598017 | 11/2005 |
|---|---|---|
| EP | 1757234 | 2/2007 |
| WO | WO95/33408 | 12/1995 |

*Primary Examiner* — Corrine M McDermott
*Assistant Examiner* — Mark Mashack
(74) *Attorney, Agent, or Firm* — Dekel Patent Ltd; David Klein (57) ABSTRACT

A suturing assembly including a first puncture element including a sharp distal end for puncturing tissue, a second puncture element including a sharp distal end for puncturing tissue, the distal ends of the first and second puncture elements being spaced from each other by a gap, suture thread disposed along a portion of the first puncture element, wherein the suture thread is arranged to be grabbed at the distal end of the first puncture element, and a suture grabber positioned at the distal end of the second puncture element.

8 Claims, 8 Drawing Sheets

(56) References Cited

U.S. PATENT DOCUMENTS

| | | | |
|---|---|---|---|
| 2007/0270885 A1* | 11/2007 | Weinert et al. | 606/139 |
| 2007/0282351 A1* | 12/2007 | Harada et al. | 606/138 |
| 2009/0018554 A1* | 1/2009 | Thorne et al. | 606/145 |
| 2009/0048613 A1* | 2/2009 | Surti | 606/139 |
| 2009/0062819 A1* | 3/2009 | Burkhart et al. | 606/148 |

* cited by examiner

SUTURING ASSEMBLY AND METHOD

FIELD OF THE INVENTION

The present invention relates generally to suturing devices and methods, such as for the percutaneous closure of body lumens and tissues by means of sutures.

BACKGROUND OF THE INVENTION

Many suturing devices are known in the art that puncture the skin with needles and percutaneously deliver sutures to the site. For example, U.S. Pat. No. 5,527,322 describes a suture applying device that includes a shaft having a nose piece attached at its distal end. The shaft and the nose piece are separated by a transition region, and a needle entry lumen in the shaft permits a flexible needle to be introduced in the distal direction. The needle is able to cross the transition region and penetrate tissue held therein and enter into a return lumen in the nose piece. The return lumen is U-shaped and acts to bend the flexible needle as it is advanced. In this way, the needle passes from the nose piece through the transition region in a proximal direction, and is able to pass through tissue within the transition region generally on the opposite side of a tissue puncture from the first suture passage. The needle then exits from the device, permitting the suture attached to the needle to be drawn fully through the device. The suture may then be tied in order to close and seal the tissue penetration.

SUMMARY OF THE INVENTION

The present invention seeks to provide an improved suturing assembly and methods, as described in more detail further below.

The assembly and methods of the present invention can be used to close a tissue puncture site with suture thread, such as a puncture site through the wall of a body lumen, or a percutaneous vascular puncture site at the distal end of a tissue tract. The assembly and methods can achieve closure wholly within the tissue tract leading to a puncture site and can be manipulated entirely from the portion of the device lying outside of the tissue tract. The present invention may be used in various medical procedures, such as but not limited to, laparoscopic procedures, endoscopic procedures, arthroscopic procedures, and the like.

There is thus provided in accordance with an embodiment of the present invention a suturing assembly including a first puncture element including a sharp distal end for puncturing tissue, a second puncture element including a sharp distal end for puncturing tissue, the distal ends of the first and second puncture elements being spaced from each other by a gap, suture thread disposed along a portion of the first puncture element, wherein the suture thread is arranged to be grabbed at the distal end of the first puncture element, and a suture grabber positioned at the distal end of the second puncture element, the suture assembly having a mode of operation wherein (a) the first puncture element punctures through a tissue wall so that the suture thread passes from a near side of the tissue wall to a far side of the tissue wall, (b) the second puncture element punctures through the tissue wall from the near side to the far side of the tissue wall, and (c) the suture grabber grabs the suture thread at the distal end of the first puncture element at the far side of the tissue wall, brings the suture thread across the gap and moves the suture thread proximally away from the distal end of the second puncture element back through to the near side of the tissue wall.

In accordance with an embodiment of the present invention the suture thread passes through a hollow portion of the first puncture element, and the suture grabber passes through a hollow portion of the second puncture element.

Further in accordance with an embodiment of the present invention the suture grabber is mounted on a cannula arranged to be moved through the second puncture element, such that as long as the cannula is inside the second puncture element, the suture grabber does not protrude out of the second puncture element, and when the slender cannula is moved distally out of the second puncture element, the suture grabber protrudes out of the second puncture element towards the suture thread at the distal end of the first puncture element.

In one exemplary embodiment, the suture grabber is biased by a biasing device, such that when the cannula is moved distally out of the second puncture element, the biasing device urges the suture grabber to protrude out of the second puncture element. In another exemplary embodiment, the suture grabber includes a resilient body, such that when the slender cannula is moved distally out of the second puncture element, spring energy of the resilient body urges the suture grabber to protrude out of the second puncture element.

The suture grabber may include a hook for grabbing the suture thread. A pull wire may be attached to the suture grabber for urging the suture grabber away from the distal end of the second puncture element.

There is also provided in accordance with an embodiment of the present invention a method for suturing including providing a first puncture element including a sharp distal end for puncturing tissue, providing a second puncture element including a sharp distal end for puncturing tissue, the distal ends of the first and second puncture elements being spaced from each other by a gap, providing suture thread disposed along a portion of the first puncture element, wherein the suture thread is arranged to be grabbed at the distal end of the first puncture element, providing a suture grabber positioned at the distal end of the second puncture element, puncturing through a tissue wall with the first puncture element so that the suture thread passes from a near side of the tissue wall to a far side of the tissue wall, puncturing through the tissue wall with the second puncture element from the near side of the tissue wall to the far side of the tissue wall, and grabbing the suture thread with the suture grabber at the distal end of the first puncture element at the far side of the tissue wall, bringing the suture thread across the gap and moving the suture thread proximally away from the distal end of the second puncture element back through to the near side of the tissue wall. Afterwards, the suture thread may be secured to form a stitch.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
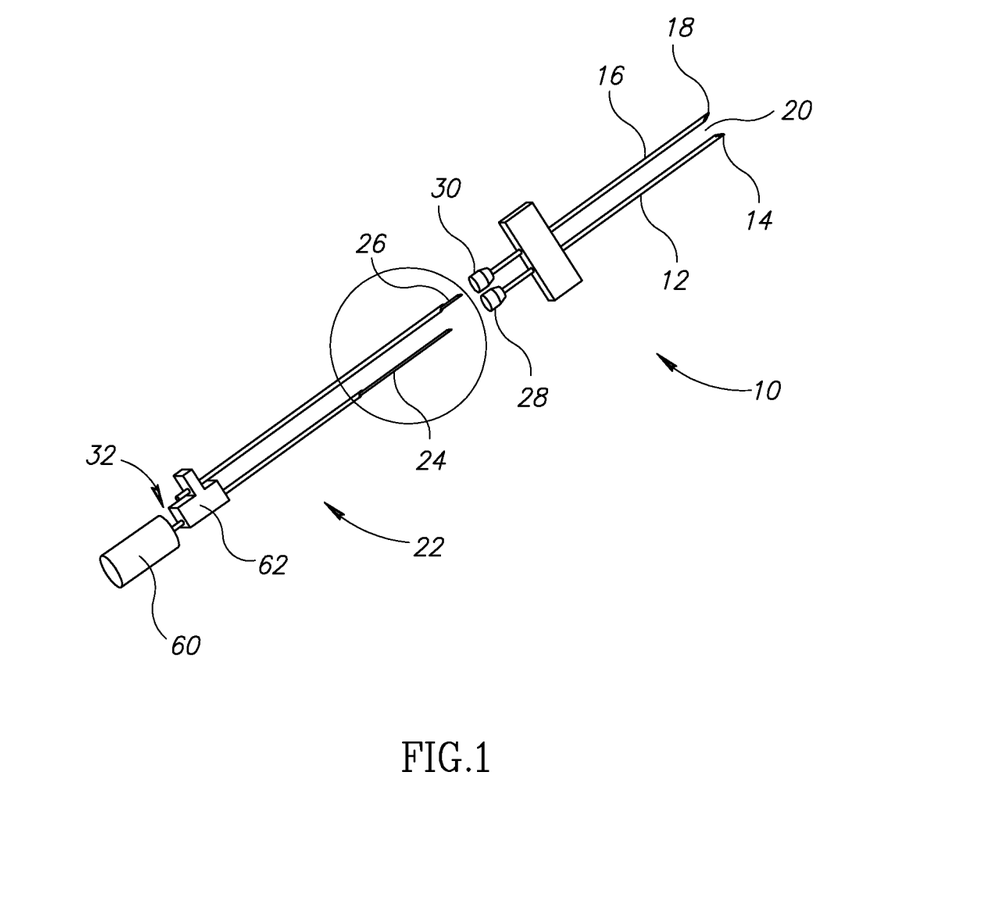
FIG. 1 is a simplified pictorial illustration of a suturing assembly, constructed and operative in accordance with an embodiment of the present invention.

Reference is now made to FIG. 1 is a simplified pictorial illustration of a suturing assembly 10, constructed and operative in accordance with a non-limiting embodiment of the present invention.

Suturing assembly 10 includes a first puncture element 12 including a sharp distal end 14 for puncturing tissue, and a second puncture element 16 including a sharp distal end 18 for puncturing tissue. The distal ends 14 and 18 of first and second puncture elements 12 and 14 are spaced from each other by a gap 20. Preferably, but not necessarily, first and second puncture elements 12 and 14 are parallel to each other.

First and second puncture elements 12 and 16 are hollow. A suture manipulating assembly 22 that includes a suture thread receiving member 24 and a suture grabber 26, which can be passed into the hollow portions of first and second puncture elements 12 and 16, respectively. First and second puncture elements 12 and 16 are provided with distal funnel cups 28 and 30, respectively, for guiding insertion of suture thread receiving member 24 and suture grabber 26. The funnel cups 28 and 30 also serve as stops to limit movement of suture thread receiving member 24 and suture grabber 26 into first and second puncture elements 12 and 16. Proximal ends of suture thread receiving member 24 and suture grabber 26 are mounted on a handle assembly 32, described more in detail hereinbelow.

Figure 2:
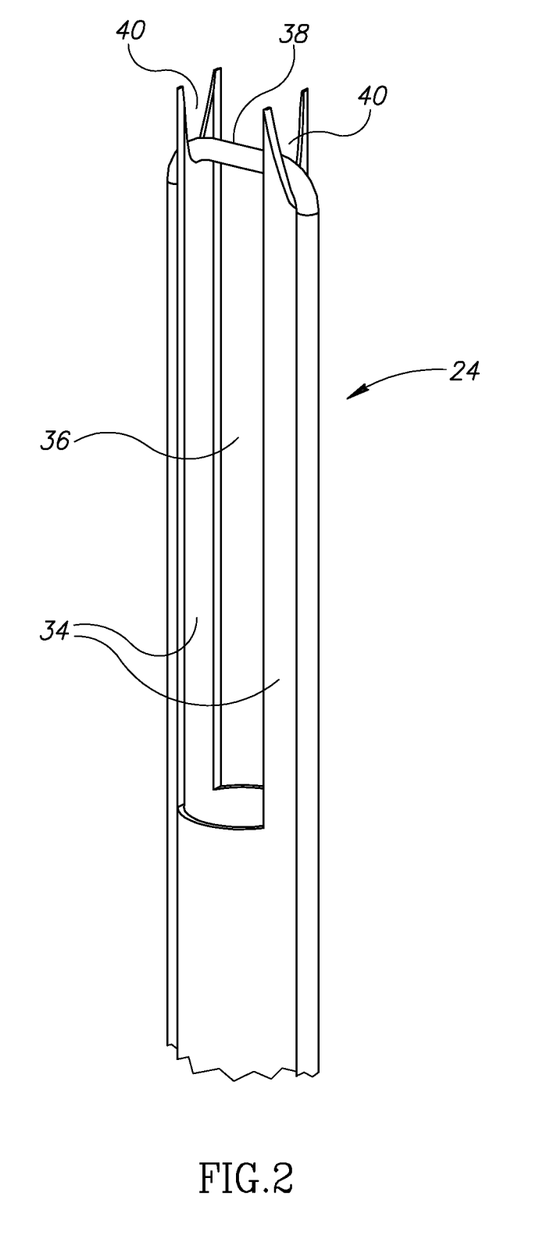
FIG. 2 is a more detailed illustration of a suture grabber used in the suturing assembly of FIG. 1, constructed and operative in accordance with an embodiment of the present invention.

Reference is now made to FIG. 2, which is a more detailed illustration of suture thread receiving member 24. In accordance with an embodiment of the present invention, a distal end of suture thread receiving member 24 includes two tines 34 separated from each other by a gap 36. Suture thread 38 sits on crevices 40 formed at the end of tines 34. Suture thread 38 may thus be doubled over suture thread receiving member 24, either along a partial length thereof or the entire length thereof. Suture thread 22 is thus arranged to be grabbed at the distal end 14 of first puncture element 12 (FIG. 1), as is explained below.

Figure 3:
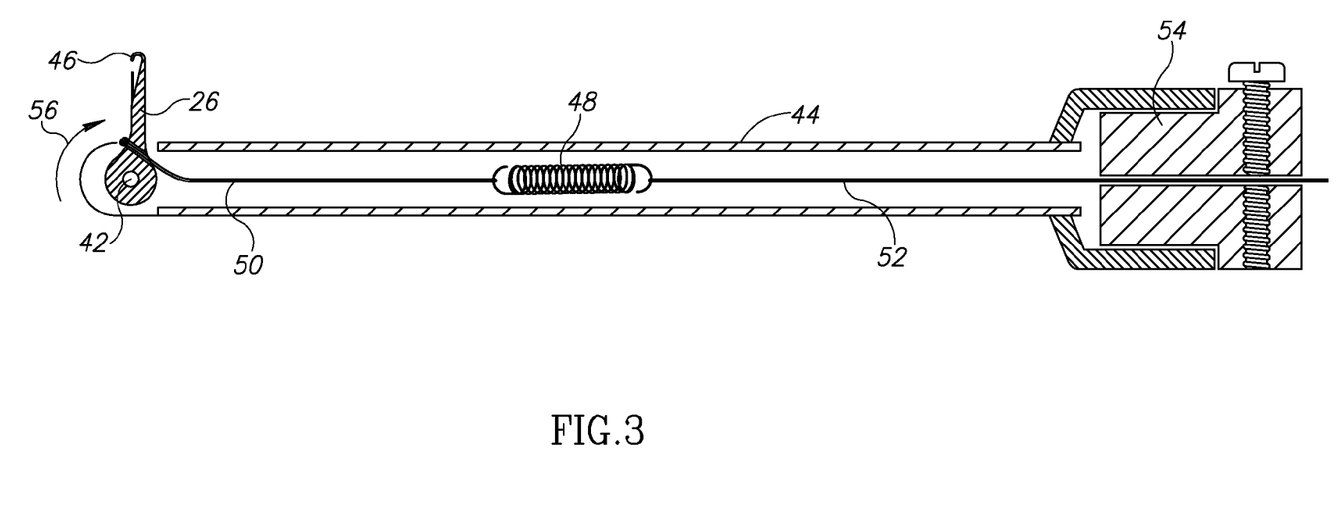
FIG. 3 is a more detailed illustration of the suture grabber.

Reference is now made to FIG. 3, which is a more detailed illustration of suture grabber 26. In accordance with an embodiment of the present invention, suture grabber 26 is pivotally mounted about a pivot 42 at a distal end of a slender cannula 44 arranged to be moved through second puncture element 16. Suture grabber 26 has a hook 46 for grabbing suture thread, as is described below. Suture grabber 26 is biased by a biasing device 48, e.g., a coil spring attached to suture grabber 26 by means of a pull wire 50 (e.g., made of nylon). The proximal end of pull wire 50 may be held in tension by a another wire 52 (e.g., made of steel) fixed to a fastener block 54.

Figure 5A:
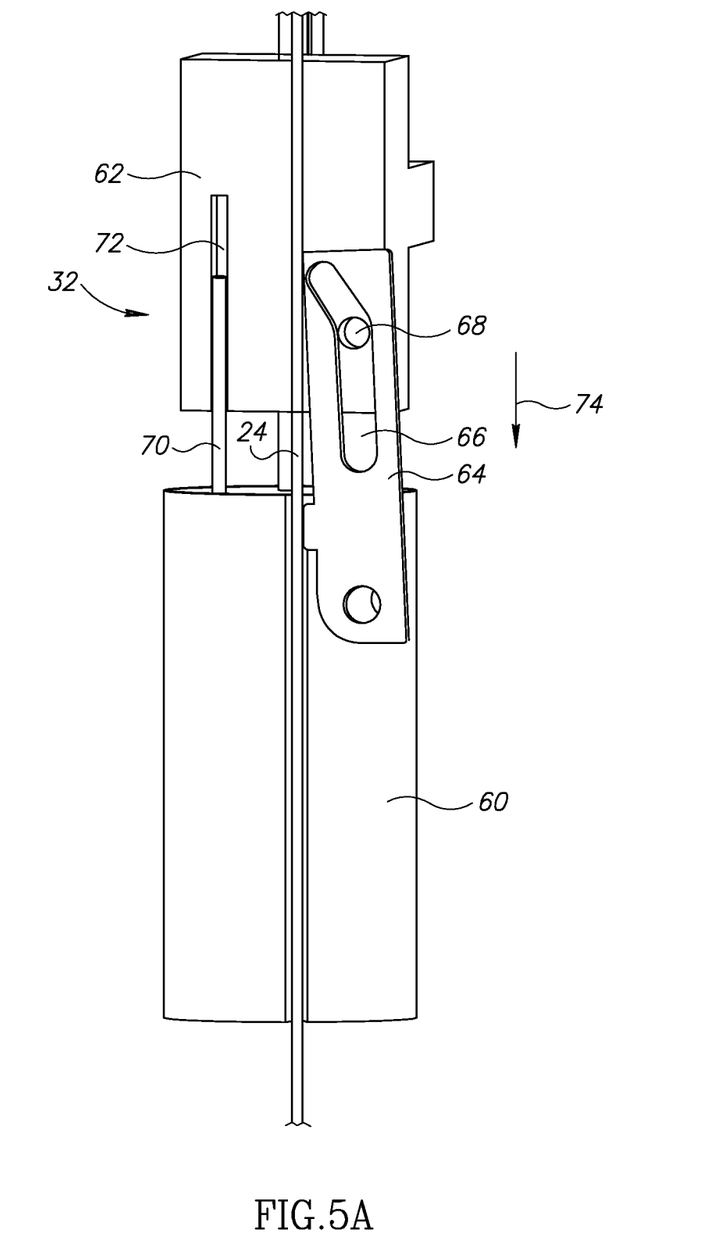
FIGS. 5A and 5B are simplified illustration of the suture thread receiving member mounted on an adjustable block of the handle assembly of the suturing assembly.

Referring now to FIG. 5A, suture thread receiving member 24 is mounted on an adjustable block 60 of handle assembly 32. Adjustable block 60 is arranged for moving with respect to a distal block 62 of handle assembly 32 by means of a latch 64 formed with a channel 66 in which is received a pin 68 mounted on distal block 62. A guide pin or wire 70 from adjustable block 60 moving in a groove 72 of distal block 62 may guide the movement of adjustable block 60 with respect to distal block 62.

Figure 4A:
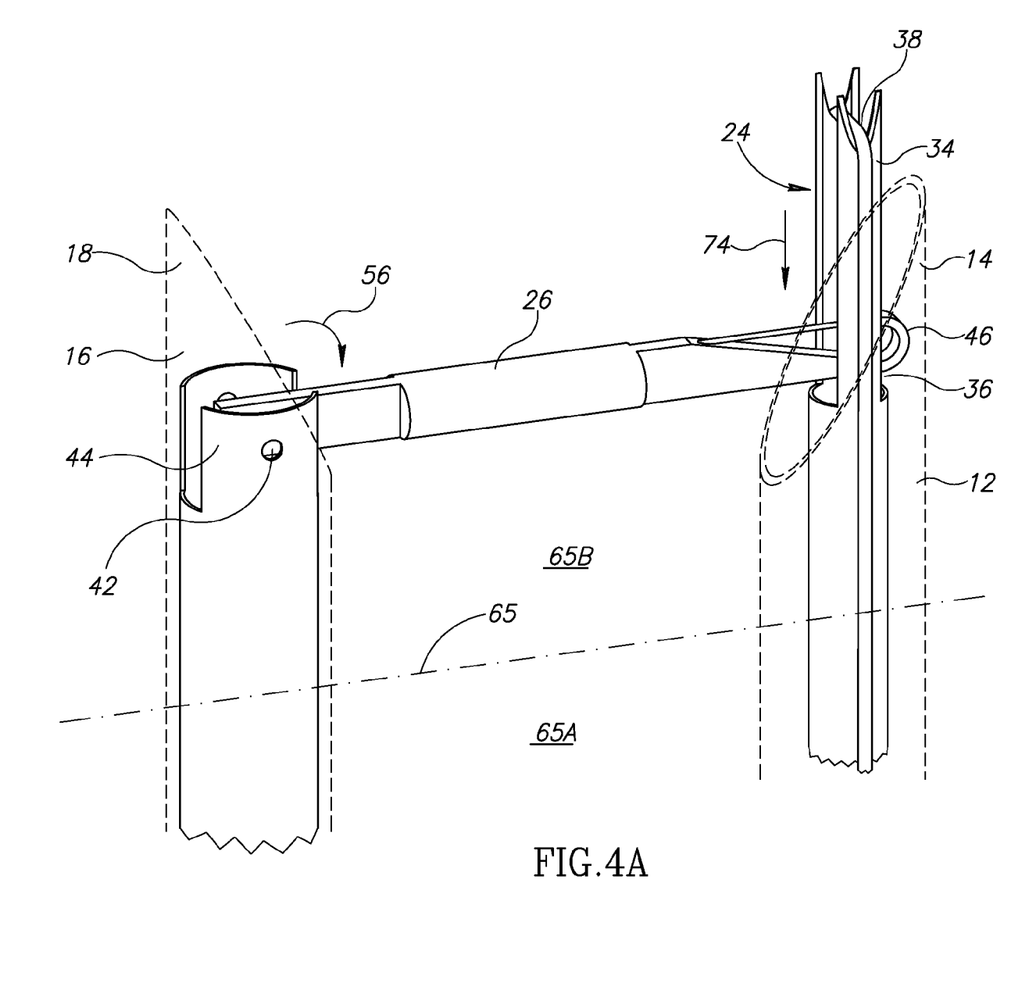
FIG. 4A is a simplified illustration of operation of the suturing assembly, wherein first and second puncture elements are pushed into tissue and sharp distal ends puncture a tissue wall.

In operation of suturing assembly 10, first and second puncture elements 12 and 16 are first pushed into tissue and the sharp distal ends 14 and 18 puncture a tissue wall 65 (FIG. 4A). Of course, in the illustrated embodiment, the first and second puncture elements 12 and 16 puncture through tissue wall 65 basically at the same time, but it is possible to construct the assembly so they are not fixed together rigidly and so they puncture the tissue wall 65 one after the other.

The suture thread receiving member 24 and suture grabber 26 of suture manipulating assembly 22 are then introduced into the hollow portions of first and second puncture elements 12 and 16, respectively. Initially, adjustable block 60 is in the position of FIG. 5A. When suture thread receiving member 24 is pushed fully up to funnel cup 28, suture thread 38 passes from a near side 65A of tissue wall 65 to a far side 65B of tissue wall 65.

As long as cannula 44 is inside second puncture element 16, suture grabber 30 is forced to lie flat with the distal end of cannula 44 and does not protrude out of second puncture element 16. However, when suture grabber 26 is pushed fully up to funnel cup 30, cannula 44 is moved distally out of second puncture element 16. At this point, the proximally-directed spring force of biasing device 48 pulls suture grabber 30 about pivot 42 in the direction of an arrow 56 (FIGS. 3 and 4A). Suture grabber 30 swings out of second puncture element 16 towards the suture thread 22 at the distal end 14 of first puncture element 12. This position is illustrated in FIG. 4A.

(As similarly mentioned above, in the illustrated embodiment, suture thread receiving member 24 and suture grabber 26 are fixed together rigidly and move together. However, they could be constructed and arranged so that suture grabber 26 is moved distally after distal movement of suture thread receiving member 24.)

Figure 4B:
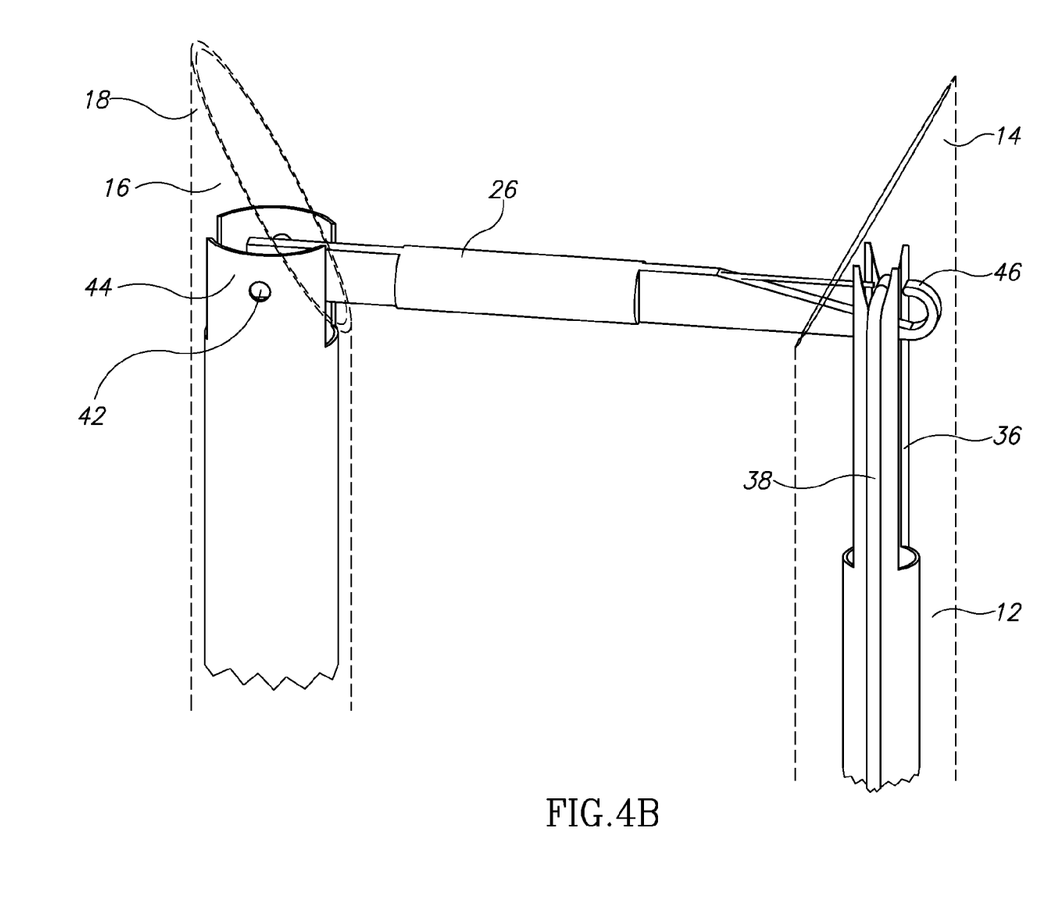
FIG. 4B is a simplified illustration of the suture thread being caught and grabbed by the suture grabber.
Figure 5B:
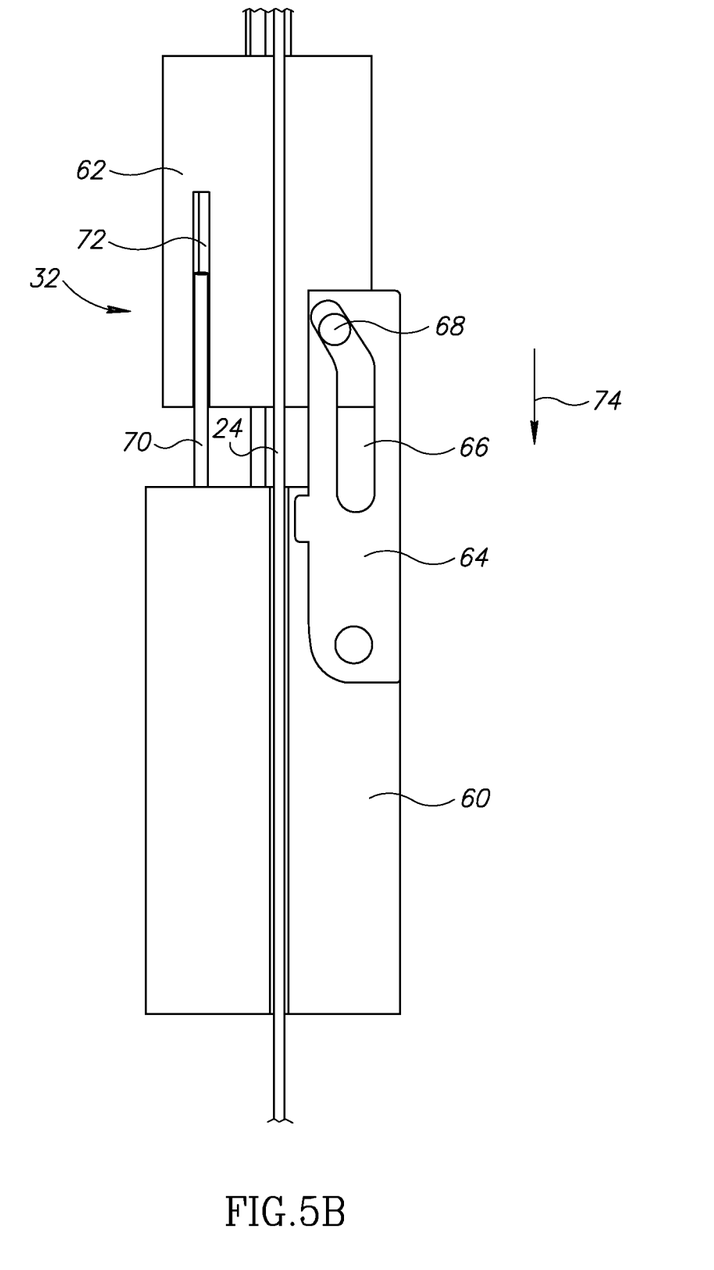
Figure 6:
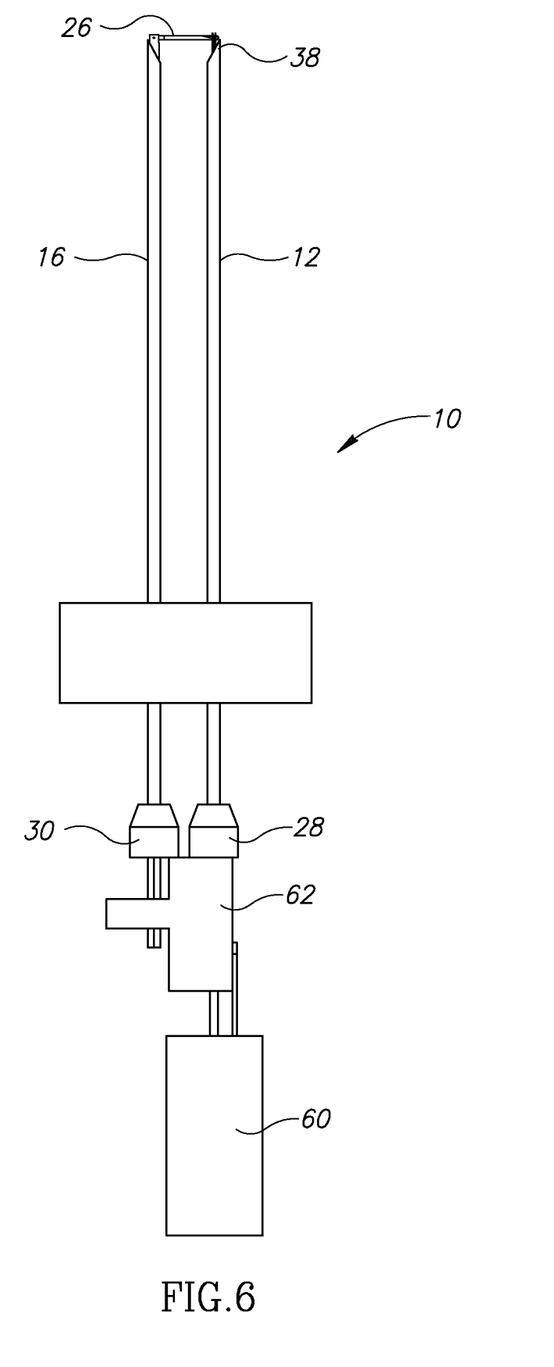
FIG. 6 is a simplified illustration of the suture thread grabbed by the suture grabber.

Referring now to FIGS. 5A and 5B, adjustable block 60 is moved proximally in the direction of an arrow 74, geometrically locking pin 68 at the end of channel 66 of latch 64. This moves suture thread receiving member 24 also in the direction of arrow 74 (FIG. 4) until suture thread 38 is caught and grabbed by suture grabber 26, as seen in FIGS. 4B and 6.

The suture thread receiving member 24 and suture grabber 26 of suture manipulating assembly 22 are then pulled proximally (backwards). This movement pulls suture grabber 26 back into second puncture element 16 (suture grabber 26 pivots to being straight with cannula 44). As suture grabber 26 moves proximally it brings along with it suture thread 38 over gap 20, proximally away from the distal end 18 of second puncture element 16, and back through to the near side 65A of tissue wall 65. Afterwards, the suture thread 38 may be secured to form a stitch.

It is noted that in another exemplary embodiment, the suture grabber may include a resilient body made of a flexible resilient material, such as but not limited to, NITINOL. In this manner, when cannula 44 is moved distally out of second puncture element 16, the spring energy of the resilient body urges suture grabber 30 to protrude out of second puncture element 16.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A suturing assembly comprising:

a first puncture element comprising a sharp distal end for puncturing tissue;

a second puncture element comprising a sharp distal end for puncturing tissue, the distal ends of said first and second puncture elements being spaced from each other by a gap;

suture thread disposed along a portion of said first puncture element, wherein said suture thread is arranged to be grabbed at the distal end of said first puncture element; and a suture grabber positioned at the distal end of said second puncture element, said suture assembly having a mode of operation wherein:

a. said first puncture element punctures through a tissue wall so that said suture thread passes from a near side of said tissue wall to a far side of said tissue wall;

b. said second puncture element punctures through the tissue wall from said near side to said far side of said tissue wall; and c. said suture grabber grabs said suture thread at the distal end of said first puncture element at the far side of said tissue wall, brings said suture thread across said gap and moves said suture thread proximally away from the distal end of said second puncture element back through to the near side of said tissue wall, wherein said suture thread is disposed on a suture thread receiving member of a suture manipulating assembly, said suture manipulating assembly being arranged to pass into hollow portions of said first and second puncture elements, said suture thread receiving member disposed in said first puncture element and comprising two tines separated from each other by another gap, wherein said suture thread is received in crevices formed at ends of said tines.

2. The suturing assembly according to claim 1, wherein said suture thread passes through a hollow portion of said first puncture element.

3. The suturing assembly according to claim 1, wherein said suture grabber passes through a hollow portion of said second puncture element.

4. The suturing assembly according to claim 3, wherein said suture grabber is mounted on a cannula arranged to be moved through said second puncture element, such that as long as said cannula is inside said second puncture element, said suture grabber does not protrude out of said second puncture element, and when said cannula is moved distally out of said second puncture element, said suture grabber protrudes out of said second puncture element towards said suture thread at the distal end of said first puncture element.

5. The suturing assembly according to claim 4, wherein said suture grabber is biased by a biasing device, such that when said cannula is moved distally out of said second puncture element, said biasing device urges said suture grabber to protrude out of said second puncture element.

6. The suturing assembly according to claim 4, wherein said suture grabber comprises a resilient body, such that when said slender cannula is moved distally out of said second puncture element, spring energy of said resilient body urges said suture grabber to protrude out of said second puncture element.

7. The suturing assembly according to claim 1, wherein said suture grabber comprises a hook for grabbing said suture thread.

8. The suturing assembly according to claim 1, wherein when said suture grabber grabs said suture thread at the distal end of said first puncture element, said suture thread is removed from said crevices.

* * * * *